(12) United States Patent
Stevens et al.

(10) Patent No.: US 8,368,894 B2
(45) Date of Patent: Feb. 5, 2013

(54) FULL-FLOW SENSOR FOR CONTAMINATION IN FLUIDS

(75) Inventors: Jed Stevens, Mission Viejo, CA (US); Gregory S. Sprenger, Colorado Springs, CO (US); Sean Sullivan, Colorado Springs, CO (US)

(73) Assignee: Velcon Filters, LLC, Colorado Springs, CO (US)

( * ) Notice: Subject to any disclaimer, the term of this patent is extended or adjusted under 35 U.S.C. 154(b) by 239 days.

(21) Appl. No.: 12/861,917

(22) Filed: Aug. 24, 2010

(65) Prior Publication Data

US 2011/0051140 A1   Mar. 3, 2011

Related U.S. Application Data

(60) Provisional application No. 61/237,102, filed on Aug. 26, 2009.

(51) Int. Cl.
*G01N 21/00* (2006.01)

(52) U.S. Cl. ......... 356/436; 356/432

(58) Field of Classification Search ......... 356/335–343
See application file for complete search history.

(56) References Cited

U.S. PATENT DOCUMENTS

| | | | |
|---|---|---|---|
| 3,511,573 A * | 5/1970 | Isreeli | 356/442 |
| 4,220,499 A * | 9/1980 | Hughes et al. | 162/49 |
| 4,492,868 A | 1/1985 | Jelvestam et al. | |
| 4,547,075 A | 10/1985 | Fei | |
| 4,746,215 A * | 5/1988 | Gross | 356/339 |
| 4,783,599 A | 11/1988 | Borden | |
| 4,906,094 A | 3/1990 | Ashida | |
| 5,033,851 A | 7/1991 | Sommer | |
| 5,061,070 A | 10/1991 | Batchelder et al. | |
| 5,739,902 A | 4/1998 | Gjelsnes et al. | |
| 5,819,373 A * | 10/1998 | Schlichter et al. | 19/205 |
| 6,151,108 A | 11/2000 | Kwon et al. | |
| 6,153,873 A | 11/2000 | Wolf | |
| 6,561,010 B2 | 5/2003 | Wilson et al. | |
| 6,710,874 B2 | 3/2004 | Mavliev | |
| 6,794,671 B2 * | 9/2004 | Nicoli et al. | 250/574 |
| 2004/0004716 A1 | 1/2004 | Mavliev | |
| 2007/0215817 A1 | 9/2007 | Shirai et al. | |
| 2008/0121026 A1 | 5/2008 | Verdegan | |
| 2009/0260324 A1 | 10/2009 | Funaki et al. | |

* cited by examiner

*Primary Examiner* — Michael P Stafira
(74) *Attorney, Agent, or Firm* — Fraser Clemens Martin & Miller LLC; J. Douglas Miller

(57) ABSTRACT

A sensing system includes a housing having an inlet for receiving a fluid flow from a source and an outlet with for directing a fluid flow from the housing, wherein a longitudinal axis transverses a center of the inlet and the outlet; a flow conduit disposed in the housing and in fluid communication with the inlet and the outlet, the flow conduit having a cross-sectional area that is substantially the same as a cross-sectional area of the inlet and the outlet, wherein a first length of the flow conduit along a second axis, and wherein the first axis and the second axis are perpendicular to the longitudinal axis; a light source for illuminating the fluid in the flow conduit along the first axis; and a sensor for detecting contaminants in the fluid.

3 Claims, 2 Drawing Sheets

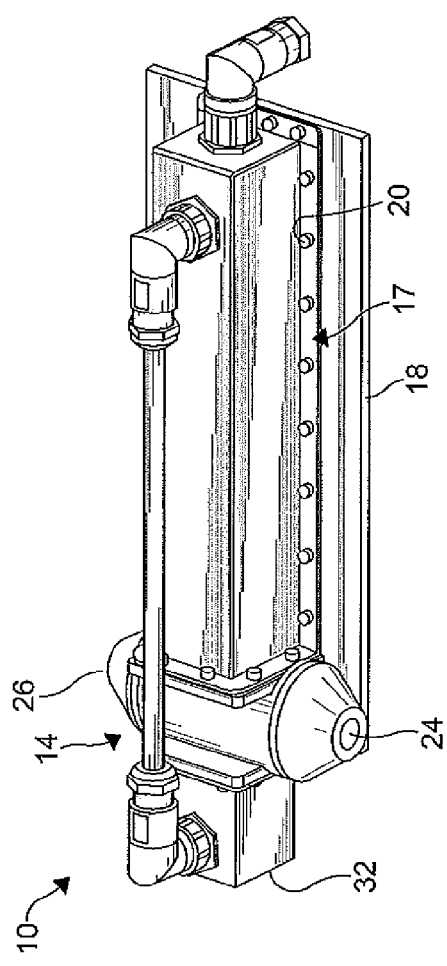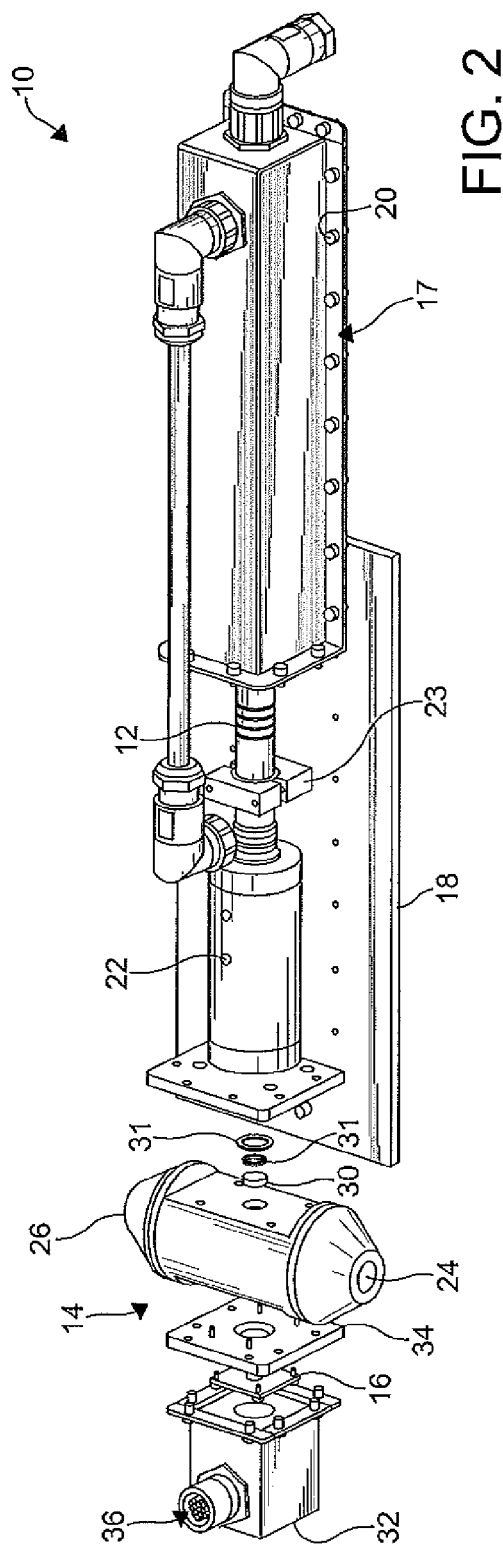

ized to emit an electromagnetic radiation with wavelengths between about 650 nm and 900 nm. It is understood that any laser or source of electromagnetic radiation can be used as desired.

FULL-FLOW SENSOR FOR CONTAMINATION IN FLUIDS

CROSS REFERENCE TO RELATED APPLICATIONS

This application is entitled to the benefit of, and claims priority to, provisional patent application Ser. No. 61/237,102 filed Aug. 26, 2009, the entire disclosure of which is incorporated herein by reference.

FIELD OF THE INVENTION

The invention generally relates to a system for sensing contaminants in transient fluids and more particularly, to a system for detecting particulate contamination in full flow fluid streams.

BACKGROUND OF THE INVENTION

Systems for sensing the presence of particulate contaminants in transient fluids have been available for many years. In order to sense small particles, the sensor is made quite small. Typically, instead of actually measuring a complete fluid stream, a sampling of the main flow of a fluid is required. In order to obtain a representative, accurate sample, kinetic sampling must be done. However, this is very difficult to accomplish in practice, because sample flow rates must be tied to full stream flow rates.

In very clean conditions, with low particle concentrations, statistical methods to tie sample measurements to the main flow provide poor correlation. In some applications, sampling is not desired. For example, where the detection of a single particle is critical, sampling and associated statistical methods cannot be tolerated. As a result, a full flow sensor is required.

It would be desirable to develop a sensor system and a method for detecting contamination in fluids, wherein the sensor system and the method provide detection of small particles with maximized flow rates.

SUMMARY OF THE INVENTION

Concordant and consistent with the present invention, a sensor system and a method for detecting contamination in fluids, wherein the sensor system and the method provide detection of small particles with maximized flow rates, has surprisingly been discovered.

Various kinds of analytical instruments are used to detect, size, and characterize small particles in fluid streams. These include both light scattering and light extinction particle-counting instruments.

Current light extinction devices have very low sensor flow rates, so that sampling of a higher flow stream is required. Typically, sensor flow rates are on the order of less than 1% of a main flow rate.

The present invention provides a sensor system which needs no sampling and allows the full flow of the stream to be continuously monitored. This is accomplished using a novel flow sensor configuration having a narrow and wide sensing zone.

In one embodiment, a sensing system comprises: a housing having an inlet with a cross-sectional area for receiving a fluid flow from a source and an outlet with a cross-sectional area for directing a fluid flow from the housing having a longitudinal axis extending through the center of the inlet and the outlet; a flow conduit disposed in the housing and in fluid communication with the inlet and the outlet, the flow conduit having a cross-sectional area that is substantially the same as the cross-sectional area of the inlet and the outlet, the flow conduit configured to cause the fluid flow therethrough to assume the shape of a ribbon having a width substantially larger than the thickness and thence configured to cause the fluid flow to exit through the outlet; a light source for illuminating the fluid in the flow conduit through the ribbon; and a sensor for sensing the light transmission through the ribbon.

The invention also provides methods for detecting contamination in a fluid.

One method comprises the steps of: providing a housing having an inlet with a cross-sectional area for receiving a fluid flow from a source and an outlet with a cross-sectional area for directing a fluid flow from the housing, wherein a longitudinal axis transverses a center of the inlet and the outlet; providing a flow conduit disposed in the housing and in fluid communication with the inlet and the outlet, the flow conduit having a cross-sectional area that is substantially the same as the cross-sectional area of the inlet and the outlet, wherein a first length of the flow conduit along a first axis is larger than a second length of the flow conduit along a second axis, and wherein the first axis and the second axis are perpendicular to the longitudinal axis of the housing; illuminating the fluid in the flow conduit along the first axis; and detecting contaminants in the fluid based upon the illumination thereof.

BRIEF DESCRIPTION OF THE DRAWINGS

The above, as well as other objects and advantages of the present invention, will become readily apparent to those skilled in the art from the following detailed description of the preferred embodiment when considered in the light of the accompanying drawings, in which:

FIG. 1 is a perspective view of a sensor system according to an embodiment of the present invention;

FIG. 2 is an enlarged exploded perspective view of the sensor system of FIG. 1;

DETAILED DESCRIPTION OF A PREFERRED EMBODIMENT OF THE INVENTION

Figure 4:
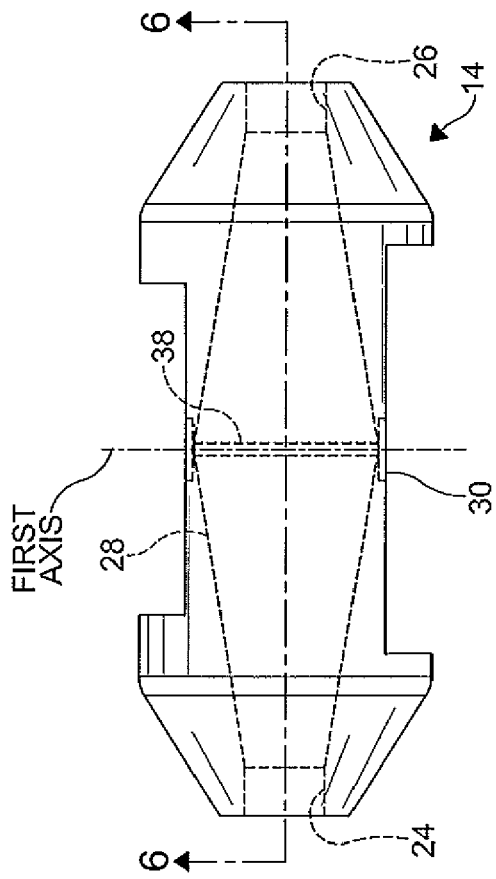
FIG. 4 is a side elevational view of the flow module of FIG. 3.
Figure 6:
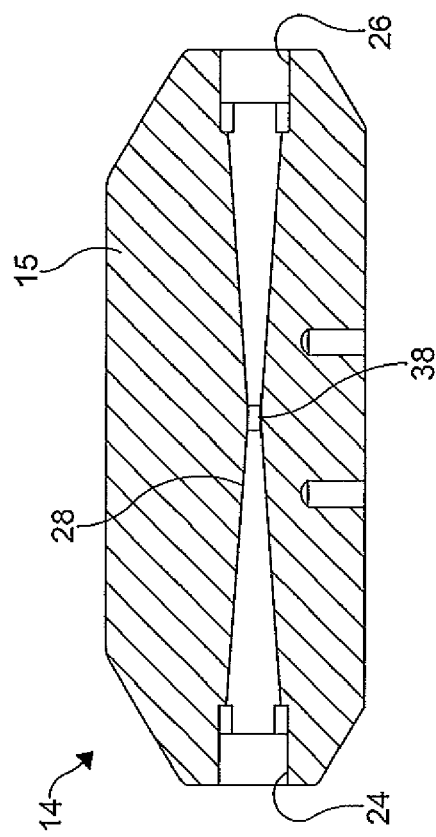
FIG. 6 is a cross sectional view of the flow module of FIG. 5 taken along line 6-6 thereof.
Figure 3:
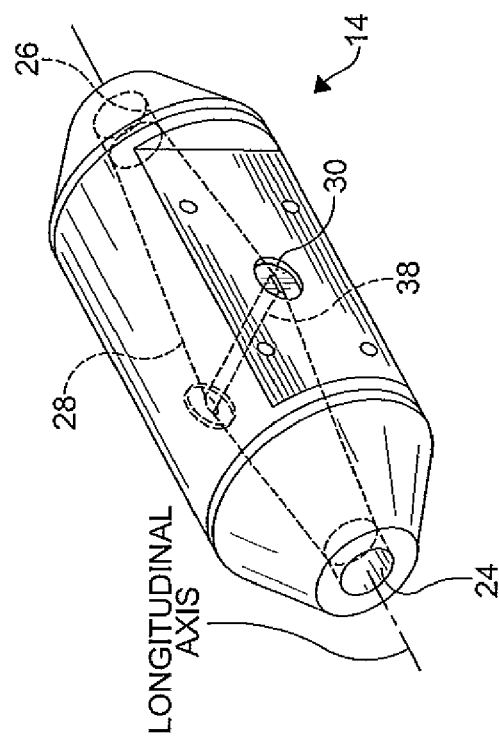
FIG. 3 is a perspective view of a flow module according to an embodiment of the present invention.

The following detailed description and appended drawings describe and illustrate the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Referring to the drawings, a sensor system 10 is illustrated according to an embodiment of the present invention. As shown, the sensor system 10 includes a laser 12, a flow module 14, and a sensor 16.

The laser 12 is enclosed in a laser housing 17, which is coupled to a laser mounting assembly 18 by a plurality of threaded fasteners 20. The laser 12 is aligned with a beam expander 22 using an industrial pivot mount 23. It is understood that the laser 12 is aligned such that a beam of electromagnetic radiation is emitted from the laser 12 and passes through the beam expander 22. Typically, the laser 12 is interconnected to a controller (not shown) for monitoring and regulating the functions thereof.

The flow module 14 clearly illustrated in FIGS. 3-6, inclusive, includes a housing 15 having an inlet 24 for receiving a fluid flow from a source (not shown) and an outlet 26 for directing a fluid flow from the housing. The housing 15 has a longitudinal axis which extends through a center of the inlet 24 and the outlet 26. A flow conduit 28 is disposed in the housing and in fluid communication with the inlet 24 and the outlet 26, which cooperate to conduct a fluid therethrough. The flow conduit 28 has a cross-sectional area that is substantially the same as the cross-sectional area of the inlet 24 and the outlet 26. It is understood that certain pipe size is required to handle a full flow upstream and downstream of the flow module 14. To maintain a full flow stream, the cross-sectional area of a downstream pipe and an upstream pipe must be similar to a cross-sectional area of the inlet 24, the outlet 26, and the flow conduit 28.

Figure 5:
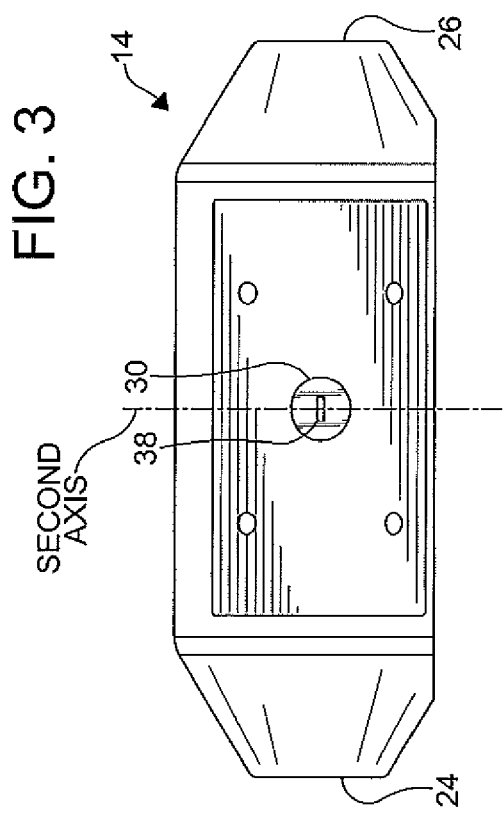
FIG. 5 is a top plan view of the flow module of FIG. 3.

In one embodiment the flow conduit 28 has a generally rhombus shape, as illustrated in FIG. 5, with a longitudinal axis extending through the center of the inlet 24 and the outlet 26. For reference, a first length is measured perpendicular to the longitudinal axis along a first axis, and a second length is measured perpendicular to the longitudinal axis along a second axis. It is understood that the first length and the second length of the flow conduit 28 along any point of the longitudinal axis are configured to maintain a constant and maximized flow of a fluid therein. In this way, the flow rate is maximized, while the dimensions of the flow conduit 28 are optimized for small particle sensing.

The flow module 14 also includes a sensing window 30 formed in the housing 15 and aligned with the beam of electromagnetic radiation emitted by the beam expander 22, so that the beam passes through a fluid in the flow conduit 28. The beam is directed through the flow conduit 28 perpendicular to the longitudinal axis thereof. It is understood that the sensing window 30 may include a fluid-tight seal such as an O-ring 31, for example.

The sensor 16 is disposed adjacent the flow module 14 to receive electromagnetic radiation passing through the flow conduit 28. In certain embodiments, the flow module 14 is directly mounted to the sensor 16 and the beam expander 22 to secure the flow module 14 and maximize alignment of the emitted beam. The sensor 16 may be a photo diode sensor enclosed in a housing 32, which is coupled to a mounting assembly 34. The sensor 16 may include a bulkhead fitting 36 for receiving electrical and communication cabling.

As clearly shown in FIGS. 3-6, a portion of the flow conduit 28, referred to as a sensing zone 38, is adapted to receive the beam of electromagnetic radiation emitted from the beam expander 22. As shown, the beam passes through the sensing zone 38 along the first axis and generally perpendicular to a direction of the fluid flow. To achieve small particle sensing, the sensing zone 38 must be kept as "narrow" as practical. In certain embodiments, the sensing zone 38 represents a portion of the flow conduit 28 having a maximum first length. Since the first length of the flow conduit 28 is maximized and the cross-sectional area of the flow conduit 28 is constant, a second length of the flow conduit 28 is minimized. For example, the inlet 24 and the outlet 26 have an inner diameter of ⅜" and the flow conduit 28 has an approximate first length of 1.7" and a second length of approximately 0.09", wherein the first length and the second length of the flow conduit 28 are measured across the sensing zone 38. However, it is understood that the inlet 24, the outlet 26, and the flow conduit 28 may have any dimensions to accommodate a full flow from the source.

In use, a fluid to be analyzed is directed through the flow module 14. Simultaneously, the laser 12 emits a beam of electromagnetic radiation into the beam expander 22. The beam exits the beam expander 22 and passes through the sensing window 30 of the flow module 14. The beam illuminates the sensing zone 38 of the flow conduit 28 for particle detection, thereby providing a means for the sensor 16 to detect contaminates in the transient fluid.

The smallest particle to be sensed by the sensing system 10 is dependent on the size of the light sensor 16 and its sensing area, and the noise of the light source (laser 12) illuminating the sensing zone 38. Currently, laser light sources are available which have noise levels <0.05%. Therefore an associated extinction sensor can sense a particle casting a shadow of approximately 0.1% of the full sensor area. For example, if the sensor area is 10 mm$^2$, the particle shadow area can be as low as 0.01 mm$^2$ or 55 microns in diameter.

It is understood that a balance is required between the three main requirements: a maximized flow rate of the fluid, a size of the smallest particle to be sensed; and a width (first length) of the flow conduit 28 across the sensing zone 38. It is further understood that the sensor system 10 may be configured to meet any desired requirements. The sensor system 10 and method require no sampling and allow the full flow of the stream to be sampled.

From the foregoing description, one ordinarily skilled in the art can easily ascertain the essential characteristics of this invention and, without departing from the spirit and scope thereof, make various changes and modifications to the invention to adapt it to various usages and conditions.

What is claimed is:

1. A sensing system comprising:
    a housing having an inlet with a cross-sectional area for receiving a fluid flow from a source and an outlet with a cross-sectional area for directing a fluid flow from the housing, wherein a longitudinal axis transverses a center of the inlet and the outlet;
    a flow conduit disposed in the housing and in fluid communication with the inlet and the outlet, the flow conduit having a cross-sectional area that is substantially the same as the cross-sectional area of the inlet and the outlet, wherein a first length of the flow conduit along a first axis is larger than a second length of the flow conduit along a second axis and the first length and the second length simultaneously vary in an inverse relationship along the longitudinal axis, and wherein the first axis and the second axis are perpendicular to the longitudinal axis of the housing and the first axis is perpendicular to the second axis;
    a light source for illuminating the fluid in the flow conduit at a portion thereof wherein the first length is at a maximum along the first axis; and
    a sensor for detecting contaminants in the fluid based upon the illumination thereof.

2. A method for detecting contamination in a fluid, the method comprising the steps of:
    providing a housing having an inlet with a cross-sectional area for receiving a fluid flow from a source and an outlet with a cross-sectional area for directing a fluid flow from the flow module, wherein a longitudinal axis transverses a center of the inlet and the outlet;
    providing a flow conduit disposed in the housing and in fluid communication with the inlet and the outlet, the flow conduit having a cross-sectional area that is substantially the same as the cross-sectional area of the inlet and the outlet, wherein a first length of the flow conduit along a first axis is larger than a second length of the flow conduit along a second axis and the first length and the second length simultaneously vary in an inverse relationship along the longitudinal axis, and wherein the first axis and the second axis are perpendicular to the longitudinal axis of the housing and the first axis is perpendicular to the second axis;

illuminating the fluid in the flow conduit at a portion thereof wherein the first length is at a maximum along the first axis; and detecting contaminants in the fluid based upon the illumination thereof.

3. A full flow system for sensing particulate contaminants in a transient fluid comprising:

a source of fluid to be sensed;

a housing having an inlet, an outlet, and an intermediate fluid conduit interconnecting the inlet and the outlet, the intermediate fluid conduit having at least a first cross-sectional area to cause the fluid flowing therethrough to assume a ribbon having a width substantially longer than a thickness, the cross-sectional area of the inlet, the outlet, and the ribbon being substantially equal to enable a full flow of fluid therethrough, and an energy transmission means for transmitting energy through the width of the ribbon of the transient fluid being sensed;

a fluid conduit interconnecting the source of fluid to be sensed to the inlet of the housing; and a detector for monitoring the energy transmitted through the width of the ribbon of fluid being sensed, the detector having a sensing area, wherein a size of the particulate contaminants sensed varies with a size of the sensing area.

* * * * *